(12) United States Patent
Pang et al.

(10) Patent No.: US 6,371,913 B2
(45) Date of Patent: Apr. 16, 2002

(54) MEDICAL DIAGNOSTIC ULTRASOUND IMAGING METHODS FOR ESTIMATING MOTION BETWEEN COMPOSITE ULTRASONIC IMAGES AND RECOVERING COLOR DOPPLER VALUES FROM COMPOSITE IMAGES

(75) Inventors: Linyong Pang, Stanford; John A. Hossack, Palo Alto; Ismayil Guracar, Redwood City, all of CA (US)

(73) Assignee: Acuson Corporation, Mountain View, CA (US)

( * ) Notice: Subject to any disclaimer, the term of this patent is extended or adjusted under 35 U.S.C. 154(b) by 0 days.

(21) Appl. No.: 09/733,131

(22) Filed: Dec. 8, 2000

Related U.S. Application Data (62) Division of application No. 09/370,060, filed on Aug. 6, 1999, now Pat. No. 6,190,321.

(51) Int. Cl.$^7$ ................................................ A61B 8/00
(52) U.S. Cl. ..................................................... 600/441
(58) Field of Search ...................... 600/437, 440–447, 600/453–457; 73/861.25; 348/163, 33; 367/7, 11, 130

(56) References Cited

U.S. PATENT DOCUMENTS

| | | |
|---|---|---|
| 5,474,073 A | 12/1995 | Schwartz et al. |
| 5,557,286 A | 9/1996 | Varadan et al. |
| 5,655,535 A | 8/1997 | Friemel et al. |
| 5,782,766 A | 7/1998 | Weng et al. |
| 5,793,883 A | 8/1998 | Kim et al. |
| 5,860,931 A * | 1/1999 | Chandler ..................... 600/458 |
| 5,873,830 A | 2/1999 | Hossack et al. |
| 5,899,861 A | 5/1999 | Friemel et al. |
| 5,910,114 A | 6/1999 | Nock et al. |
| 5,910,119 A * | 6/1999 | Lin ............................. 600/455 |
| 5,928,151 A | 7/1999 | Hossack et al. |
| 5,980,459 A | 11/1999 | Chiao et al. |
| 6,126,598 A | 10/2000 | Entrekin et al. |
| 6,131,458 A | 10/2000 | Langdon et al. |

OTHER PUBLICATIONS

McCann et al., Multidimensional Ultrasonic Imaging for Cardiology, Proceedings of the IEEE, vol. 76, No. 9, Sep. 1998, pp. 1063–1072.

* cited by examiner

Primary Examiner—Marvin M. Lateef
Assistant Examiner—Ali M. Imam
(74) Attorney, Agent, or Firm—Brinks Hofer Gilson & Lione

(57) ABSTRACT

An medical diagnostic ultrasonic image processing method estimates motion between first and second composite ultrasonic images that include both B-mode and Color Doppler information. First and second B-mode images are extracted from the first and second composite ultrasonic images, respectively, and then motion is estimated between the first and second B-mode images. The estimated motion is then used to compose a multi-frame image using at least portions of the composite ultrasonic images or derivatives of the composite ultrasonic images, such as the B-mode images.

5 Claims, 5 Drawing Sheets

MEDICAL DIAGNOSTIC ULTRASOUND IMAGING METHODS FOR ESTIMATING MOTION BETWEEN COMPOSITE ULTRASONIC IMAGES AND RECOVERING COLOR DOPPLER VALUES FROM COMPOSITE IMAGES

This application is a continuation division of application Ser. No. 09/370,060, filed Aug. 6, 1999, U.S. Pat. No. 6,190,321.

BACKGROUND

This invention is related to medical diagnostic ultrasound imaging, and more specifically to methods for estimating motion between composite ultrasound images and recovering Color Doppler values from composite images.

Several extended field of view methods have recently been proposed. See the discussions in Weng U.S. Pat. No. 5,782,766; Weng U.S. Pat. No. 5,557,286; Hossack U.S. patent application Ser. No. 09/196,986; and Sumanaweera U.S. patent application Ser. No. 09/196,987. The two above-referenced U.S. patent applications are assigned to the assignee of the present invention.

These patent documents disclose several different methods for registering and composing an extended field of view image. In all cases, substantially coplanar images are sequentially acquired as the transducer moves along the patient's body parallel to the azimuthal direction. Selected ones of these images are compared with one another to provide transducer motion estimates, and these transducer motion estimates and then used to compose portions of multiple ones of the acquired images to form the desired extended field of view.

Weng U.S. Pat. No. 5,782,766 discusses the superposition of images comprising color-coded Doppler velocity or Doppler energy images. In the disclosed system, the motion estimation is performed on a B-mode image, prior to the time the B-mode image is combined with the Color Doppler image. This approach is not well-suited for use in the situation where the Color Doppler image has already been combined with the B-mode image. This is because speckle correlation methods do not operate on Color Doppler images with optimum effectiveness. Color Doppler data, unlike the speckle of B-mode data, are not motion invariant. This limitation may represent a significant disadvantage in some circumstances, for instance in off-line review stations where only the composite B-mode/Color Doppler image is available.

SUMMARY

By way of introduction, the preferred methods described below perform extended field of view or 3-D imaging on composite ultrasound images by first extracting the underlying B-mode images from the composite images and then performing image correlation on the extracted B-mode images to estimate motion. After the relative motion vectors have been determined, selected components of the composite images (B-mode, Color Doppler, or composite B-mode/Color Doppler) are registered using the determined motion vectors and then composed to form the desired extended field of view or 3-D image. In this way, extended field of view and 3-D imaging are made possible from composite color ultrasound images (i.e., mixed-mode images).

The foregoing paragraph has been provided by way of introduction only, and is not intended to limit the scope of the following claims.

DETAILED DESCRIPTION OF THE PRESENTLY PREFERRED EMBODIMENTS

A. General Discussion

In extended field of view (EFOV) imaging, multiple substantially coplanar ultrasound images are sequentially acquired as the transducer is moved across the body surface in the azimuthal direction. Any two adjacent images in this sequence of images will have an overlapping area. This overlapping area can be used to register the two images with respect to one another using any of various image registration methods, such as image correlation. After registration, the desired EFOV image is composed using portions of the originally acquired images, registered according to their relative positions. When the originally acquired images include Color Doppler data, it is preferable to separate B-mode data from Color Doppler data and to perform motion estimation on the B-mode data alone. The reason for this is that features of the B-mode image (including, for example, features such as speckle of the B-mode image) are functions of position and are therefore well adapted for use in registering images. Color Doppler data on the other hand are not only functions of space but also functions of other variables, such as time, velocity or energy. Color Doppler data values will change even without transducer motion when they are acquired at different times.

Typically, an ultrasound imaging system acquires a complete frame of B-mode data and a partial frame of Color Doppler data. Depending upon the level of Doppler energy and/or velocity, particular pixels of B-mode image data are overwritten or mixed with Color Doppler values to form a composite frame.

In one common implementation, Color Doppler data is already superimposed on B-mode data before the composite image is captured and saved for extended field of view imaging. For example, composite image video frames are captured and compressed as JPEG images and then stored using a format such as the medical imaging standard DICOM. The stored DICOM images represent the ultrasound image after scan conversion, and include both B-mode data and Color Doppler data, if the frame includes Color Doppler data. In these cases, only the composite images are available for estimating transducer motion in extended field of view imaging.

The preferred embodiments described below separate the B-mode image data including speckle from the composite image. Then the B-mode image data are used for motion estimation. Finally, any desired component of the original composite image is used to compose the desired extended field of view image. Since the B-mode speckle image has been extracted from the composite, mixed-mode image, the B-mode speckle image, the pure Color Doppler image, the original composite image, or a new composite image formed with a different composing method (e.g., the color overwrite method) can be composed to form an extended field of view image.

There are two popular Color Doppler modes commonly used on ultrasound imaging systems: velocity mode and energy mode. In the velocity mode, the absolute value of the Color Doppler data indicates the speed of the fluid motion, while the sign of the Color Doppler data indicates the direction of motion. In the energy mode, the value of the Color Doppler data indicates the value of Doppler energy, and all data are positive. The methods commonly used to mix Color Doppler data with B-mode data are slightly different for the velocity and energy modes, and preferably B-mode extraction techniques are used that are appropriate for the specific Color Doppler mode in use on the composite images being processed.

B. Specific Embodiments

Figure 1:
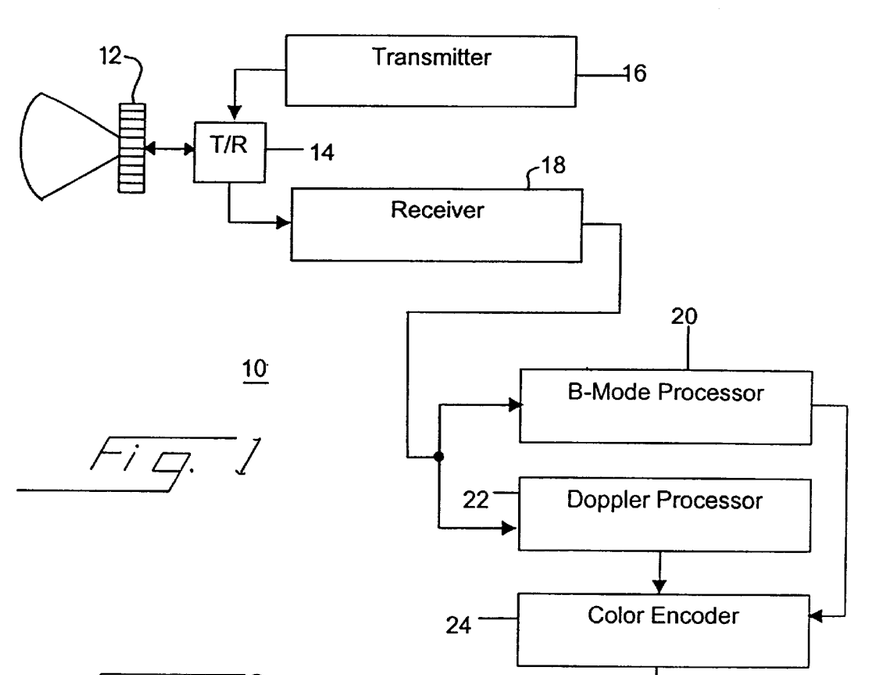
FIG. 1 is a block diagram of a medical diagnostic ultrasound imaging system that generates composite images including both B-mode (intensity) image data and Color Doppler (velocity or energy) image data.
Figure 2:
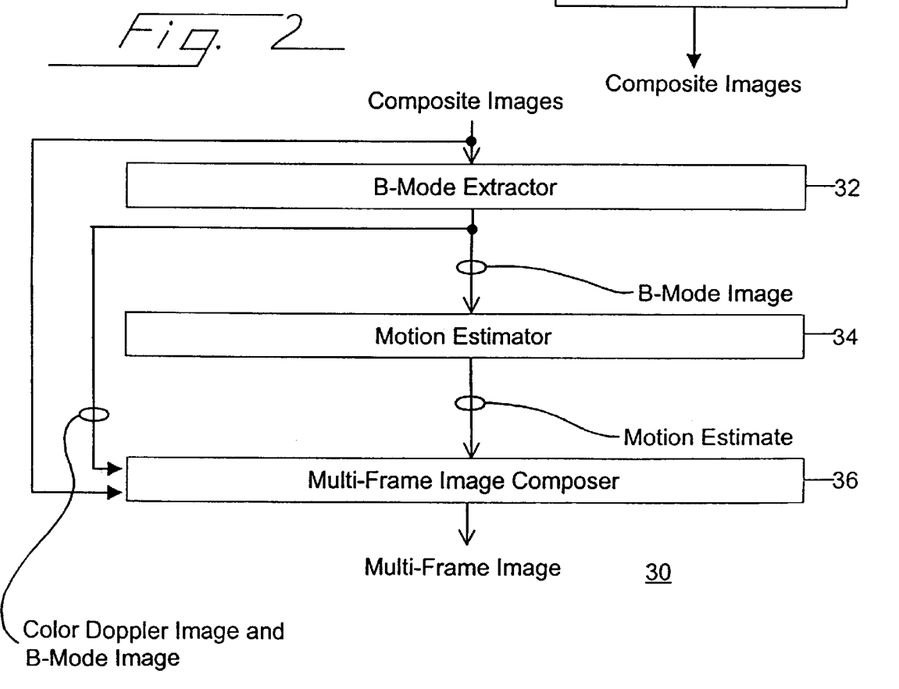
FIG. 2 is a block diagram of an image processing system that implements a preferred embodiment of this invention.

Turning now to the drawings, FIGS. 1 and 2 provide block diagrams of a medical diagnostic ultrasound imaging system 10 and an image processor 30, respectively.

The system 10 of FIG. 1 includes a transducer probe 12 that is connected by a transmit/receive switch 14 both to a transmitter 16 and to a receiver 18. The transmitter 16 applies transducer waveforms to the transducer probe 12, thereby causing the transducer probe 12 to emit beams of ultrasonic energy directed along selected scan lines. Returning echoes from the tissue being imaged impinge upon the transducer probe 12, which generates transducer signals in response thereto that are applied to the receiver 18. In this example, the transducer probe 12 includes a phased array transducer, and the transmitter 16 and the receiver 18 include respective beamformers. The beamformer of the transmitter 16 supplies transmit waveforms that are controlled in amplitude and phasing to cause the ultrasonic energy transmitted by the transducer probe 12 to add coherently along the desired scan line. The beamformer of the receiver 16 delays the respective transducer signals as appropriate such that they add coherently along the desired scan line.

The receiver waveforms generated by the receiver 18 are applied in parallel to a B-mode processor 20 and a Doppler processor 22. The B-mode processor 20 produces output signals indicative of the intensity of the reflected echoes along the selected scan line, and the Doppler processor 22 produces output signals indicative of a Doppler parameter such as Doppler velocity or Doppler energy along the selected scan line.

The B-mode signals and the Doppler-mode signals from the processors 20, 22 are applied as inputs to a color encoder 24 that generates a composite image. The composite image includes (1) B-mode image data at pixels where there is no Doppler image data and (2) either Doppler image data or a blending of Doppler image data and B-mode image data at pixels where Doppler image data is available.

Figure 6:
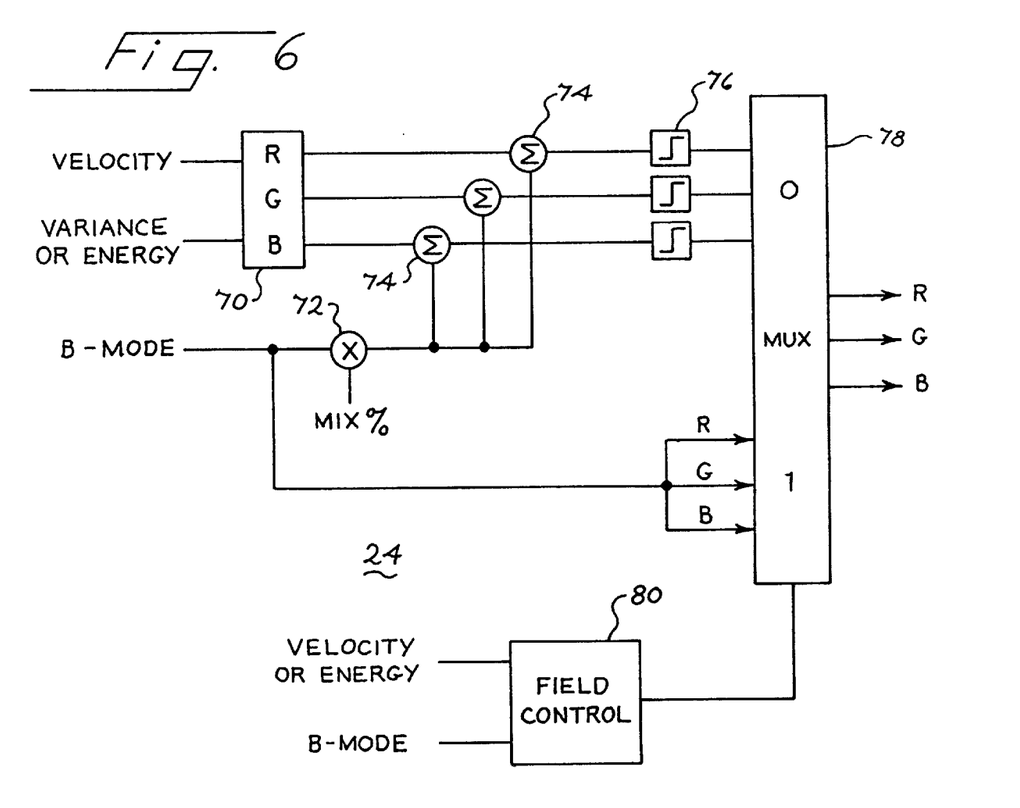
FIG. 6 is a block diagram of the color encoder 24 of FIG. 1.

FIG. 6 provides a more detailed block diagram of one exemplary form that the color encoder 24 can take. In this embodiment, the Color Doppler data (velocity or energy) is applied as an addressing input to a color map 70 that stores color values associated with the respective addressing input. In this example, the color values correspond to amplitude values for red, green and blue channels, though of course color values in other systems can be used.

The color encoder 24 also receives as an input a B-mode signal that is scaled at a multiplier 72. The scaled B-mode value is then combined via summers 74 with the three color values generated by the color map 70. The output signals from the summers 74 are limited to extreme values by limiters 76 and then applied as inputs to a multiplexer 78. The unscaled B-mode values are applied via a second set of inputs to the multiplexer 78. The B-mode image is color coded as a gray scale image in this embodiment, and the red, green and blue color values for the B-mode image are therefore equal to one another at any given pixel. The multiplexer 78 is controlled by a field control 80 to pass either the blended Color Doppler/B-mode color values form the limiters 76 or the gray scale B-mode values.

The color map 70 can be taken as one example of the color map $C_{org}$ discussed below, and the output signals from the limiter 76 can be taken as one example of composite color values $V_{comp}$ described below. The scaled B-mode components described above can be taken as an example of gray scale components included in the composite color values $V_{comp}$.

The ultrasonic imaging system 10 can be completely conventional, and many alternatives are possible. Analog or digital signal processing techniques can be used for the various components, and any suitable transducer probe can be used. Mechanically-steered, single-element transducers can be used, as well as the phased arrays discussed above. When phased arrays are used, 1-, 1.5-, and 2-dimensional arrays can be used, including both linear and curvilinear arrays. As a non-limiting example, the transmitter, receiver, B-mode processor, and Doppler processor described in the following U.S. patents can be used: U.S. Pat. Nos. 5,675,554; 5,827,188; and 5,555,534.

The composite images generated by the color encoder 24 can be stored in any suitable medium using any desired format. For example, the composite images may be stored as DICOM images on a hard disk, magnetic tape or the like.

FIG. 2 provides a block diagram of an image processor 30 that operates to form an extended field of view image from the composite images of FIG. 1. The processor 30 includes a B-mode extractor 32, a motion estimator 34, and a multi-frame image composer 36.

The B-mode extractor 32 accepts as inputs the composite images described above and then extracts B-mode images from the respective composite images. The B-mode extractor 32 can operate using the methods described below in conjunction with FIG. 4.

The motion estimator accepts as an input the B-mode images from the B-mode extractor 32 and compares selected B-mode images to determine the motion therebetween. The motion estimator 34 can use any of a variety of techniques for estimating the relative motion between selected images, such as those described in the patent documents referenced in the background portion of this specification.

The multi-frame image composer 36 accepts as inputs the motion estimates from the motion estimator 34, the B-mode images from the B-mode extractor 32, and the original composite images. The composer 36 uses the motion estimates to register selected frames. Portions of the registered frames are then combined to form the desired multi-frame image, which in this embodiment is an extended field of view image. The composer 36 may alternately register images in a 3-D data set. Because both the composite images and the B-mode images are provided to the composer 36, the multi-frame image can be composed from appropriate portions of the original composite images, the B-mode images, Doppler-mode images obtained by subtracting the B-mode images from the composite images, or any desired blending of the B-mode images and the Doppler-mode images.

Figure 5:
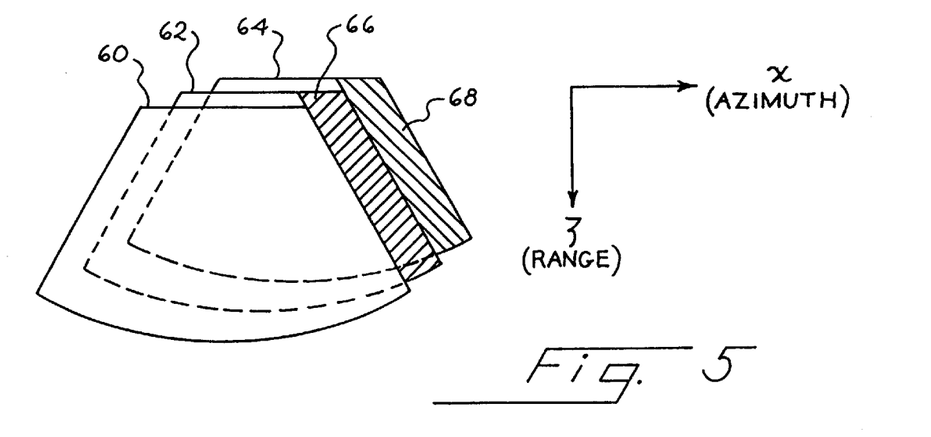
FIG. 5 is a schematic diagram illustrating how portions of three acquired images are composed to form an extended field of view image.

FIG. 5 provides a schematic representation of the formation of a multi-frame image by the composer 36. In FIG. 5, three composite image frames 60, 62, 64 are shown. In actual practice, the frames 60, 62, 64 are substantially coplanar, though they have been shown in staggered relationship in FIG. 5 for clarity of illustration. The composer 36 uses the motion estimates to register the frames 60, 62, 64. Then strips 66, 68 from the frames 62, 64, respectively, are combined with the original frame 60 to form the desired extended field of view.

Figure 3:
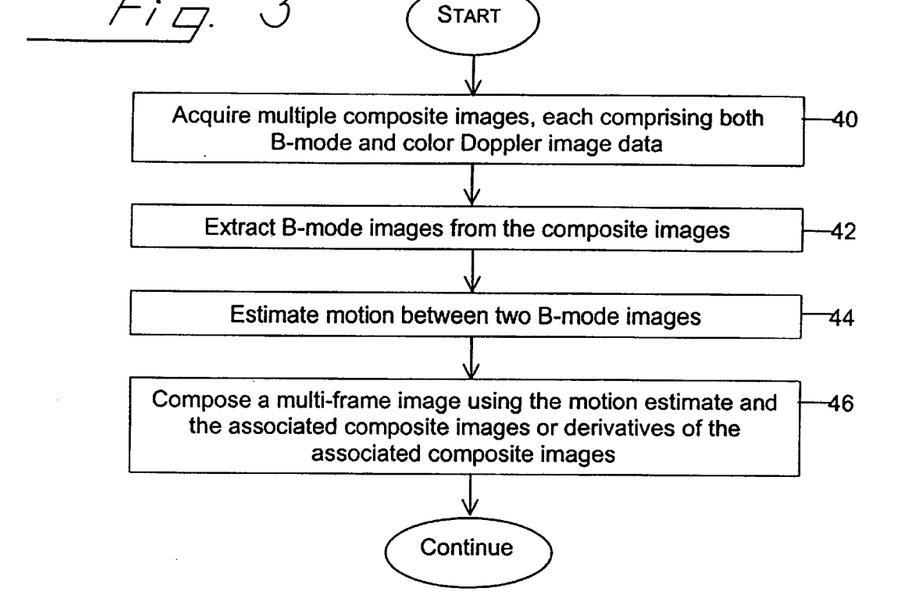
FIG. 3 is a flow chart of a method performed by the image processor of FIG. 2.

FIG. 3 provides a flow chart of a preferred method implemented by the processor 30 of FIG. 2. First, multiple composite images are acquired at 40. Each composite image comprises both B-mode image data and Color Doppler image data. Next, B-mode images are extracted from the composite images at 42, using for example the methods described below in conjunction with FIGS. 4 and 7. Next, motion is estimated at 44 between two selected ones of the B-mode images, and finally a multi-frame image such as an extended field of view image is composed using the motion estimates from 44. The multi-frame image can use the original composite images from 40, the extracted B-mode images from 42, or other derivatives of the composite images. For example, the B-mode image data can be stripped from the composite image data to form Color Doppler image data that are used for the multi-frame image.

Figure 4:
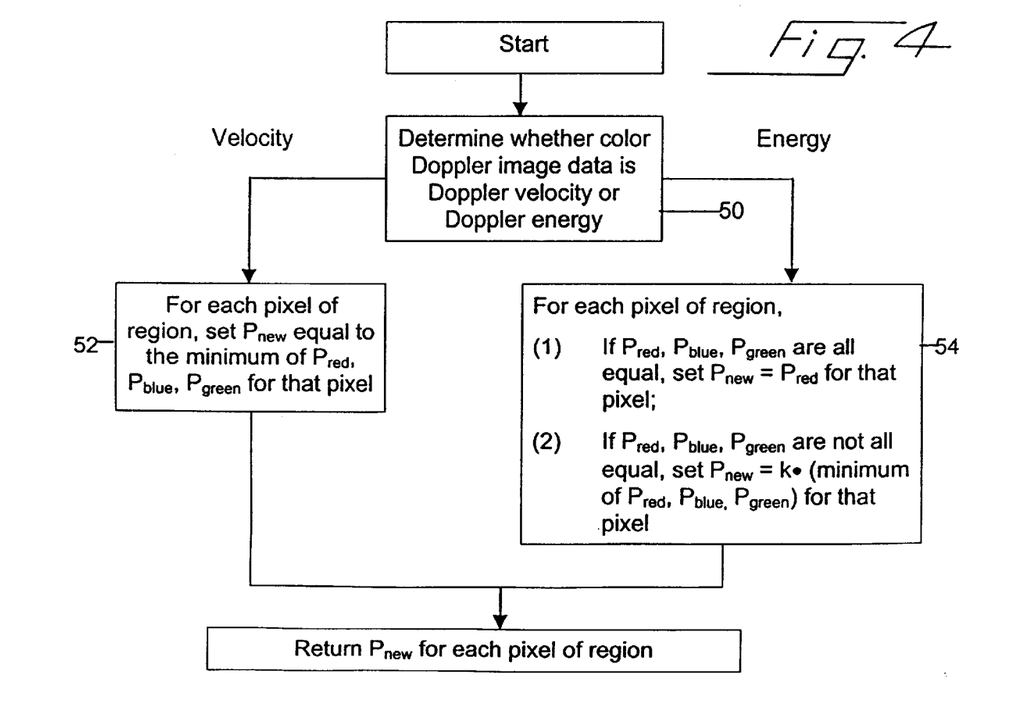
FIG. 4 is a more detailed block diagram of a portion of the method of FIG. 3.

FIG. 4 provides a more detailed flow chart of a first method for extracting B-mode images from composite images. In FIG. 4, first the composite image is checked at 50 to determine whether the Color Doppler image data included in the composite image is representative of Doppler velocity or Doppler energy. In this example, different algorithms are used to extract B-mode image data for these two different possibilities. This determination can be made from the header of the composite image file.

When the composite image Color Doppler image data represents Doppler velocity, two color channels from the three available color channels are generally used for representing each velocity value. For example, in one commonly used system, the three basic color channels correspond to red, green and blue, and only two of these color channels are used to represent velocity values. In some cases, the velocity color map for both positive and negative velocities uses the same set of two color channels. In other cases, the velocity color map for positive velocities uses a first set of two color channels, while the velocity color map for negative velocities uses another set of two color channels. Typically, when a pixel of the composite image includes Color Doppler velocity information, the Color Doppler velocity value is applied as an input to a color table that generates corresponding color RGB values. These RGB values are then added to the B-mode gray scale values. Thus, if a pixel is representative of B-mode image data only, the RGB values of each pixel are equal, If a particular pixel includes both B-mode image and Color Doppler velocity data, then the minimum color value corresponds to the B-mode image data.

As shown at 52, when the composite image includes Color Doppler velocity values, each pixel of the region is set equal to the minimum of the three color values for that pixel. In the notation of 52, $P_{new}$ corresponds to the B-mode image data for a pixel extracted from the original composite image data for that pixel. $P_{red}$, $P_{blue}$, and $P_{green}$ represent the three color values for the associated pixel.

In the event the composite image is found to include Color Doppler energy values, a different algorithm is preferably used. This is because Color Doppler energy image data is often combined with B-mode image data in a different manner in the composite image. A target that reflects a high-amplitude Color Doppler energy signal often reflects a high-amplitude B-mode signal as well. For this reason, the B-mode image data are preferably compressed (for example, from 0–256 to 0–64) prior to formation of the composite signal to avoid overflow. Since Color Doppler energy data does not have negative values, two color channels are generally sufficient for color coding Doppler energy image values. In one conventional system, the whole range of color is not used for each color channel. For instance, if 24-bit RGB color is used, color levels 0 through 195 in each color channel are used for the Doppler energy color table. The other 64 levels are left for B-mode data to avoid overflow in color superimposing. If the Doppler energy value is 0, the composite image is generated by using the B-mode image value for the pixel value of the composite image. If the Doppler energy value is not 0, it is passed to a color lookup table to find its corresponding RGB color. Then, the B-mode image data is compressed (for instance, from 0–255 to 0–63) and added to the color value to form the composite image.

As shown at 54 in FIG. 4, for each pixel of a region including Doppler energy image data the extracted B-mode pixel value $P_{new}$ is set to one of the three color values $P_{red}$, $P_{blue}$, $P_{green}$ in the event all three color values are equal. Alternatively, if $P_{red}$, $P_{blue}$ and $P_{green}$ are not all equal (indicating the presence of Doppler energy image data in this pixel), then the extracted B-mode image data $P_{new}$ is set equal to the minimum color value (the minimum of $P_{red}$, $P_{blue}$, $P_{green}$) for that pixel scaled by a factor K. The factor K is used to expand the minimum color value to the full range (0–255 in this example). In one example, the scale factor can equal 4. The B-mode extractor flow chart in FIG. 4 returns the B-mode pixel values $P_{new}$ for each pixel of the region from which the B-mode image was extracted.

Any suitable approach can be used to implement the methods of FIGS. 3 and 4. For example, the elements 32, 34, 36 can be implemented as a properly programmed digital computer. Any suitable computer hardware and any suitable programming language can be used, as appropriate for the particular application.

Figure 7:
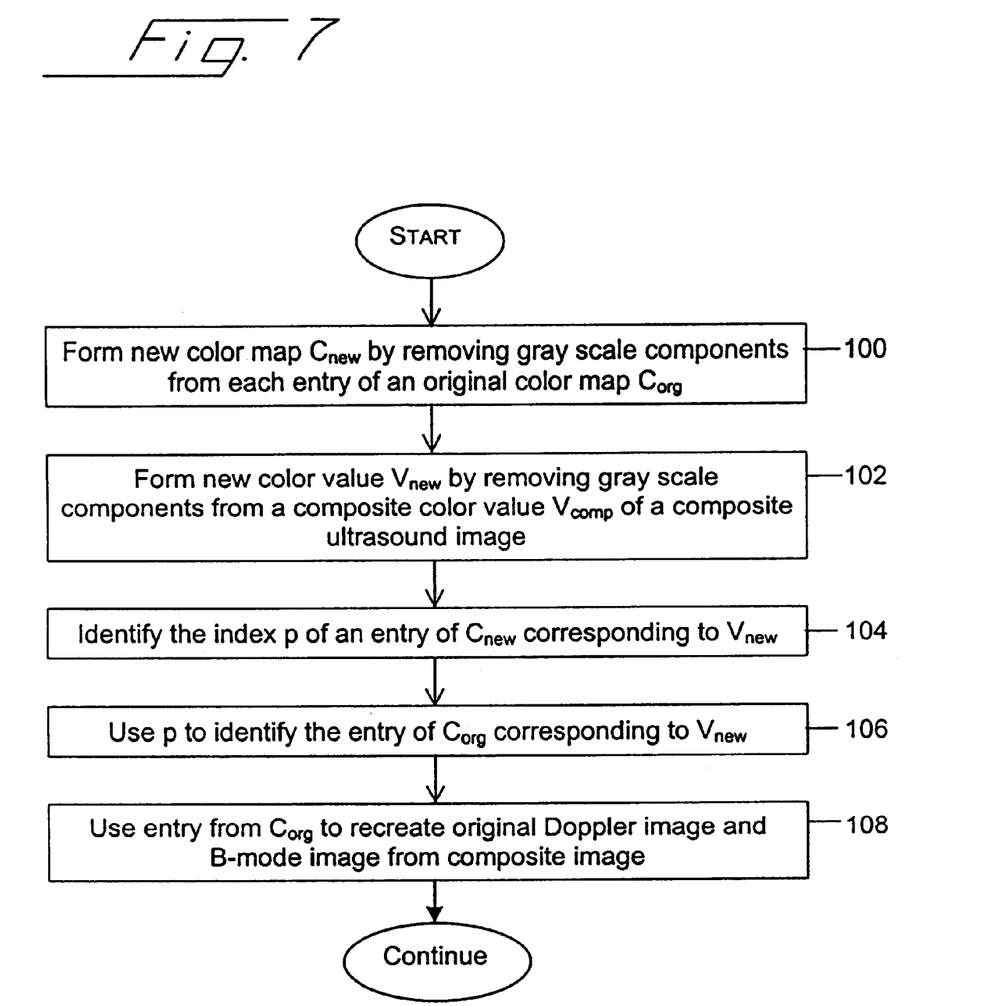
FIGS. 7 and 8 are flow charts of methods performed by the image processor of FIG. 2.

In a second preferred embodiment, the image processor 30 of FIG. 2 operates to extract the Color Doppler image from the composite image using a particularly efficient extraction method. A preferred method for extracting Color Doppler image information is flow charted in FIG. 7. This preferred method works with many conventional color maps, and in general is useful with arbitrary color maps that use three channels for each entry of the color map, where no two entries in the color map are the same color with different saturation levels. That is, all entries of the color map satisfy the following condition:

$$\begin{bmatrix} R_{org}(m) \\ G_{org}(m) \\ B_{org}(m) \end{bmatrix} - \begin{bmatrix} R_{org}(n) \\ G_{org}(n) \\ B_{org}(n) \end{bmatrix} \neq C \begin{bmatrix} 1 \\ 1 \\ 1 \end{bmatrix}, \quad \text{(Eq. 1)}$$

In Equation 1, $R_{org}(m)$, $G_{org}(m)$, and $B_{org}(m)$ correspond to the red, green and blue color values for the $M^{th}$ entry of the original color map $C_{org}$, and C is an arbitrary constant.

At block 100 in the method of FIG. 7, a new color map $C_{new}$ is generated from the original color map $C_{org}$ by removing gray scale components at each entry of the original color map $C_{org}$. Using the notation of Equation 2 for the color values of each entry of the original color map $C_{org}$, each entry of the new color map $C_{new}$ is defined by Equation 3.

$$C_{org}(n) = (R_{org}(n), G_{org}(n), B_{org}(n)) \quad \text{(Eq. 2)}$$

$$\begin{bmatrix} R_{new}(n) \\ G_{new}(n) \\ B_{new}(n) \end{bmatrix} = \begin{bmatrix} R_{org}(n) \\ G_{org}(n) \\ B_{org}(n) \end{bmatrix} - \min(R_{org}(n), G_{org}(n), B_{org}(n)) \begin{bmatrix} 1 \\ 1 \\ 1 \end{bmatrix} \quad \text{(Eq. 3)}$$

That is, for each entry of the original color map $C_{org}$, the minimum value of the three color values for that entry is subtracted from each of the three color values for that entry. In that the subtracted amount has an equal value for each color, the subtracted amount is equal to the largest gray scale component of the original entry of the color map $C_{org}$.

Next, at block 102 in FIG. 7, a new color value $V_{new}$ is formed from a given composite color value $V_{comp}$ by removing the gray scale components from the composite color value $V_{comp}$. As shown in Equation 4, the composite color value $V_{comp}$ includes three component color values $R_{comp}$, $G_{comp}$, $B_{comp}$. $V_{new}$ is obtained by subtracting the minimum of $R_{comp}$, $G_{comp}$, $B_{comp}$ from each of these three color values.

$$V_{new} = \begin{bmatrix} R_{comp} \\ G_{comp} \\ B_{comp} \end{bmatrix} - \min(R_{comp}, G_{comp}, B_{comp}) \begin{bmatrix} 1 \\ 1 \\ 1 \end{bmatrix} \quad \text{(Eq. 4)}$$

In effect, the largest gray scale component has been removed from $V_{comp}$ to form $V_{new}$.

At block 104 in FIG. 7, the index p is identified for the entry of the new color map $C_{new}$ that corresponds to $V_{new}$. Many alternative approaches can be used for this identification. For example, the sum of absolute differences for all three channels of each entry of the new color map $C_{new}$ can be examined to find the single entry having the minimum sum of absolute differences for all three channels as compared with $V_{new}$. In the case where there is no color loss during image capture, storage and retrieval, this minimum should be zero if $V_{new}$ corresponds to a $C_{new}$. Alternately, in the case of color loss such as that associated with JPEG compression, if this minimum sum of absolute difference is less than the threshold such as 10, then the corresponding entry can be identified with $V_{new}$. A more preferred approach is described below in conjunction with FIG. 8. This more preferred approach substantially reduces the time required to identify the index p.

Continuing with FIG. 7, at block 106 the index p is used to identify the entry of the original color map $C_{org}$ corresponding to $V_{new}$. At block 108, the entry from the original color map $C_{org}$ identified in block 106 is used to recreate the original Color Doppler image on a pixel-by-pixel basis from the composite image that was used as the starting point.

Once the Color Doppler image data have been recovered, it is a simple matter to recover the B-mode speckle image data based on the original composite image data, using an algorithm appropriate for the mixing mode that was used to form the composite image.

Once the original Color Doppler and B-mode image have been extracted from the composite image, the techniques described above can be used to compose any desired multi-frame image using the motion estimate determined from the extracted B-mode image and any desired combination of the extracted B-mode image and the extracted Color Doppler image. For example, the multi-frame image can be formed using B-mode image data only, Color Doppler image data only, or any desired composite form of B-mode image data and Color Doppler image data.

Figure 8:
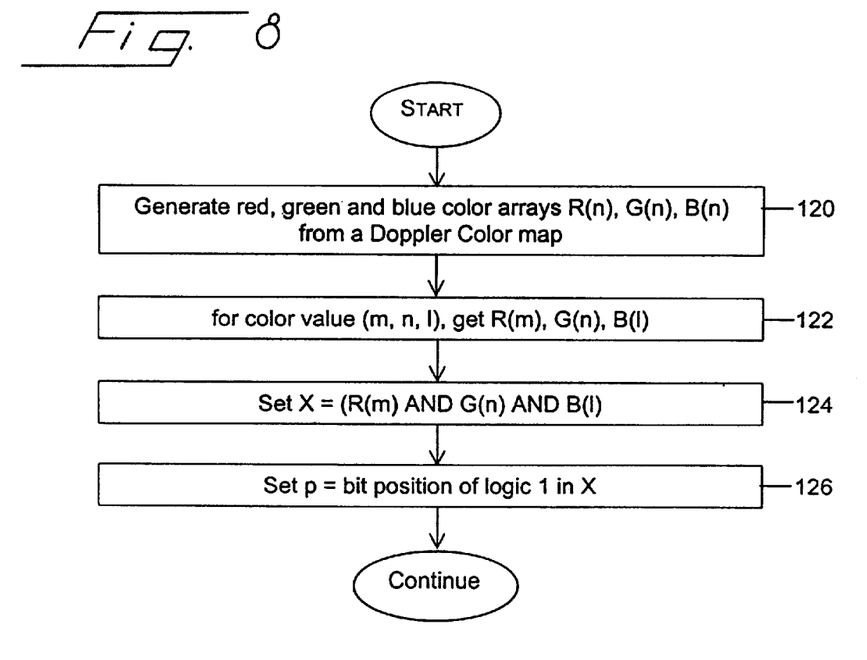
Figure 9:
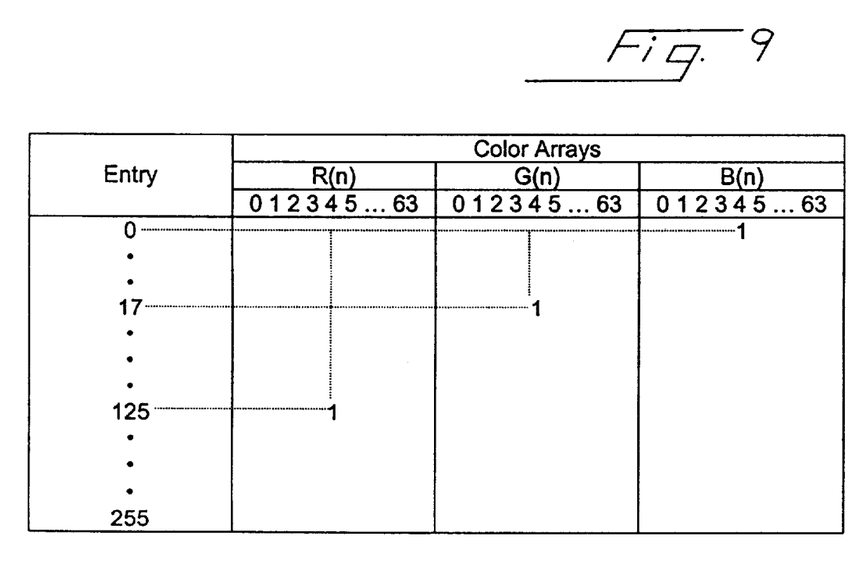
FIG. 9 is a schematic diagram of one example of three color arrays used in the method of FIG. 8.

Turning to FIG. 8, a preferred method for identifying the entry of a color map corresponding to a given color value is described in flow chart form. First, red, green and blue color arrays R(n), G(n), B(n) are generated from a given Doppler color map, as indicated at block 120. In this example, the Color Doppler values have 64 different levels, each color array includes 256 entries, and each entry includes a respective 64-bit integer. Other array sizes are of course possible. In this example, each entry represents a respective color level and each bit in each entry indicates whether the corresponding one of the 64 entries of the corresponding color map matches this color. FIG. 9 provides one example, in which the three color arrays R(n), G(n), B(n) are shown as three columns of 256 separate entries. Each entry has 64 bits, with bit 0 corresponding to the $0_{th}$ entry of the corresponding color map, bit 1 corresponding to the first entry of the corresponding color map, and so forth. By way of example, it will be assumed that the fifth entry of the corresponding color map has the color value 125, 17, 0. That is, the fifth bit from the left of R(125) is equal to 1; the fifth bit from the left of G(17) is equal to 1; and the fifth bit from the left of B(0) is equal to 1. Of course, the color arrays will include 1 in many other locations in the various entries, as appropriate for the other 63 entries of the color array. Composite images are often stored in JPEG format, which may cause some color value offsets in each channel. In order to account for such offsets caused by JPEG compression and decompression, it is preferred to set neighboring bits in the illustrated entries and adjacent entries equal to 1. The color arrays of FIG. 9 need to be created only once for each separate color map.

Returning to FIG. 8, at block 122 a color value (m, n, l) is used to extract the $m^{th}$ entry of the red color array, the $n^{th}$ entry of the green color array and the $l^{th}$ entry of the blue color array. At 124, the selected entries of the three color arrays are compared with one another in a bit AND operation to generate a variable X. The location of the bit of variable X that is equal to 1 after this bit AND operation identifies the value of p, and p identifies the corresponding entry in the color map from which the color arrays were created.

By way of example, assuming the composite color value $V_{comp}$ is equal to (128, 20, 3), then the minimum value of $V_{comp}$ is equal to 3, and $V_{new}$ is equal to (125, 17, 0). Using the example of FIG. 9, it is the fifth entry of the color map $C_{new}$ that corresponds to $V_{new}$, because R(125), G(17) and B(0) all have bit 5 set equal to 1. Thus, $C_{new}(5)$ is the entry of $C_{new}$ that corresponds to $V_{new}$, and $C_{org}(5)$ is the entry of $C_{org}$ that corresponds to the Color Doppler component of $V_{comp}$.

There are several conventional methods that can be used at block 126 to identify the bit position of logic 1 in the variable X. For example, a loop can be performed in which X is left-shifted by one position in each cycle of the loop. When the leftmost bit of the shifted version of the variable X is equal to 1, the number of loop cycle times is equal to p. Another method to locate the logic 1 bit in X is to use a conventional divide and conquer method. All of these operations can be implemented using MMX technology to take advantage of the 64-bit operation of MMX processors. The method of FIG. 8 is substantially faster than a conventional method as defined initially above.

As before, any suitable processor and programming techniques can be used to implement the basic functions illustrated in FIGS. 7 and 8.

C. Alternatives

Of course, many alternatives are possible to the preferred embodiments described above. The B-mode extraction techniques, the Color Doppler extraction techniques, the color map entry identification techniques, the motion estimation techniques, the composition techniques can all be varied as appropriate for the particular application, and can be used alone or in various sub-combinations and combinations.

In many applications it will be preferable to form a multi-frame image that includes Color Doppler image data by using composite images from a single phase of the cardiac cycle for the EFOV image. This is because in many cases tissue positions and velocity values change dramatically from one part of the cardiac cycle to another. By building the entire extended field of view image from composite images acquired at a single phase of the cardiac cycle, such variations are reduced or minimized. U.S. patent application Ser. No. 60/114,194, filed Dec. 30, 1998, and assigned to the assignee of the present invention, is hereby incorporated by reference in its entirety for its teaching of methods for implementing extended field of view images of this type. As explained above, the present invention provides methods for recovering the original Color Doppler values from a composite image. These Color Doppler values can be used to detect a selected phase of the cardiac cycle, thereby eliminating the need for EKG triggering devices when single-phased images are acquired.

In general, it has been found that motion estimation errors are reduced by using a larger number of gray scale levels in the extracted B-mode image. However, when the number of gray scale levels is as low as 16, the average motion estimation error is only about 0.15% of a pixel width in translation and 0.00046 in in-plane rotation. Thus, adequate motion estimation can be performed even with relatively coarsely graduated B-mode images, i.e. the B-mode images obtained from composite Color Doppler energy images, in which the B-mode values of the composite images are compressed.

A different method can be used to compose B-mode and Color Doppler components for the multi-frame image than that used in the original composite images from which the B-mode and Color Doppler components were derived. For example, Color Doppler components may be combined with finite opacity to create a filtered look and to suppress artifactual lines between successive images.

It should be apparent from the foregoing that an improved medical diagnostic ultrasonic imaging processing method has been described. Stored composite images can be registered and composed to form an extended field of view image, and the accuracy of motion estimation is insensitive to the position of pixels incorporating Color Doppler image information in the composite image or the number of such pixels.

As used herein, the term "frame" and the associated image data are intended to encompass all or part of a full frame. For example, the B-mode extractor 32 can extract B-mode image data for all or part of a full frame.

The term "multi-frame image" is intended to refer to a composite image in which at least parts of multiple image frames are combined to form the multi-frame image. The term encompasses extended field of view images, various types of images derived from 3-D data sets, as well as the multi-frame images discussed in U.S. patent application Ser. No. 09/196,986, the text of which is hereby incorporated by reference.

The term "color value" is intended broadly to encompass a color intensity value in any desired color coding scheme, such as RGB, YUV and other color coding schemes.

The foregoing detailed description has discussed only a few of the many forms that this invention can take. For this reason, this detailed description is intended only by way of illustration and not limitation. It is only the following claims, including all equivalents, that are intended to define the scope of this invention.

What is claimed is:

1. A method for identifying an entry in a Color Doppler map of a medical diagnostic ultrasonic processing system, said method comprising:

(a) generating first, second and third color arrays from a Doppler color map of a medical diagnostic ultrasonic imaging processing system, each color array associated with a respective color and comprising a plurality of color array entries, each color array entry associated with a respective color value and indicative of the Doppler color map entries that are associated with the respective color value;

(b) for a color (m, n, I), comparing the entry of the first color array associated with the $m^{th}$ color value, the entry of the second color array associated with the $n^{th}$ color value, and the entry of the third color array associated with the $I^{th}$ color value to identify the Doppler color map entry associated with the color (m, n, I).

2. The method of claim 1 wherein act (b) comprises the act of bit AND the entry of the first color array associated with the $m^{th}$ color value, the entry of the second color array associated with the $n^{th}$ color value, and the entry of the third color array associated with the $I^{th}$ color value.

3. A medical diagnostic ultrasonic image processing method for extracting a-Color Doppler image from a composite ultrasonic image comprising an array of composite color values, said method comprising:

(a) removing a gray scale component from each entry of a first color map associated with the composite ultrasonic image to form a second color map;

(b) removing a gray scale component from one of the composite color values of the composite ultrasonic image to form a new color value; and (c) identifying an entry of the second color map corresponding to the new color value.

4. The method of claim 3 wherein each entry of the first color map comprises respective red, green and blue values.

5. The method of claim 4 wherein each gray scale component has equal red, green and blue values.

* * * * *